United States Patent [19]

Bloom et al.

[11] Patent Number: Plant 7,344

[45] Date of Patent: Oct. 2, 1990

[54] BERGENIA "BRESSINGHAM RUBY"

[75] Inventors: Alan H. Bloom; Adrian J. Bloom, both of Diss, England

[73] Assignee: Blooms of Bressingham Ltd., Bressingham, England

[21] Appl. No.: 386,182

[22] Filed: Jul. 28, 1989

[51] Int. Cl.[5] ..... A01H 5/00

[52] U.S. Cl. ..... Plt./68

[58] Field of Search ..... Plt./54, 68

*Primary Examiner*—James R. Feyrer

*Attorney, Agent, or Firm*—Keith D. Gehr

[57] ABSTRACT

A new and distinct variety of Bergenia characterized by its distinct winter foliage color.

3 Drawing Sheets

The present invention relates to a new and distinct hybrid of Bergenia which originated as a cross-pollination of *Bergenia purpurascens* and *Bergenia cordifolia* in the Saxifragaceae family.

The new Bergenia is the result of open cross-pollination of the plants listed above at Blooms of Bressingham's nursery in Bressingham, Diss, Norfolk, England. This new hybrid was selected from a large number of seedlings. The mother plant of this new variety was isolated for further evaluation due to its unique seasonal foliage color change. This new variety has been reproduced by asexual propagation (division and tissue culture). Each of the progeny exhibits identical characteristics to the original mother plant establishing this hybrid as reproducible and true to type. The plant will not reproduce true from seed.

This new hybrid is unlike any Bergenia commercially available nor like any of those described by Bailey, Blooms, Brown, Busse, Harper, Horn, Still or Walters (see reference list) as evidenced by the following unique characteristic:

(1) Attractive winter foliage color over entire leaf surface and petioles.

(2) During early winter (December and January), the foliage changes from a rich green color to a deep brown. In later winter (February), the foliage color intensifies to a burgundy red color.

BRIEF DESCRIPTION OF THE PHOTOGRAPHS

DETAILED PLANT DESCRIPTION

The following is a detailed description of the new Bergenia hybrid based on observations of specimen plants grown in Bressingham, England and in Federal Way, Washington. The color determinations are all based on The Royal Horticultural Society Colour Chart.

Overall size and growth habit

*Size.*—The ultimate size of the new variety is 15 to 30 cm (6 to 12 in) tall with a spread of 60 cm (24 in). The Bergenia is a herbaceous perennial which spreads by rhizomes and can be used as a ground cover or in a perennial border.

Foliage:

*Type.*—Evergreen, herbaceous (can die back to ground in a hard winter).

*Shape.*—Oval to orbicular.

*Length.*—10 to 25 cm (4 to 10 in).

*Width.*—7 to 22 cm (3 to 8.5 in).

*Petiole length.*—2.5 to 8 cm (1 to 3 in).

*Margins.*—Slightly crenate.

*Apex.*—Rounded (broadly obtuse).

*Base.*—Rounded but Cuneate.

*Texture.*—Glabrous, semi-glossy.

*Leaf arrangement.*—Originate from common point on crown.

*Venation.*—Compound pinnate.

Flower:

*Petal count.*—5 petals.

*Petal shape.*—Entire margin; spatulate; claw with blade.

*Flower type.*—Complete; simple.

*Flower size.*—2 to 2.5 cm (0.75 to 1 in).

*Blooming habit.*—Panicle which is 20 to 48 cm (8 to 19 in) tall.

*Bloom period.*—Late March through May.

Color Characteristics:

Foliage:

*Mature leaves upper surface.*—Spring: R.H.S. Colour Chart Fan 3, Green Group, No. 143 A. Winter: December and January: R.H.S. Colour Chart Fan 4, Brown Group, No. 200 A. February and March: R.H.S. Colour Chart Fan 4, Greyed - Purple Group, No. 187 A.

*Mature leaves lower surface.*—Spring: R.H.S. Colour Chart Fan 3, Green Group, No. 144 B. Winter: R.H.S. Colour Chart Fan 4, Greyed-Purple Group, No. 187 A and 183 C. Veins: R.H.S. Colour Chart Fan 2, Red-Purple Group, No. 59 B.

Flowers: R.H.S. Colour Chart Fan 2, Red-Purple Group, No. 72 C.

DESCRIPTION OF PARENT PLANTS

This Bergenia hybrid has characteristics which makes it unique from its parents: *B. purpurescens* and *B. cordifolia.*

Figure 1:
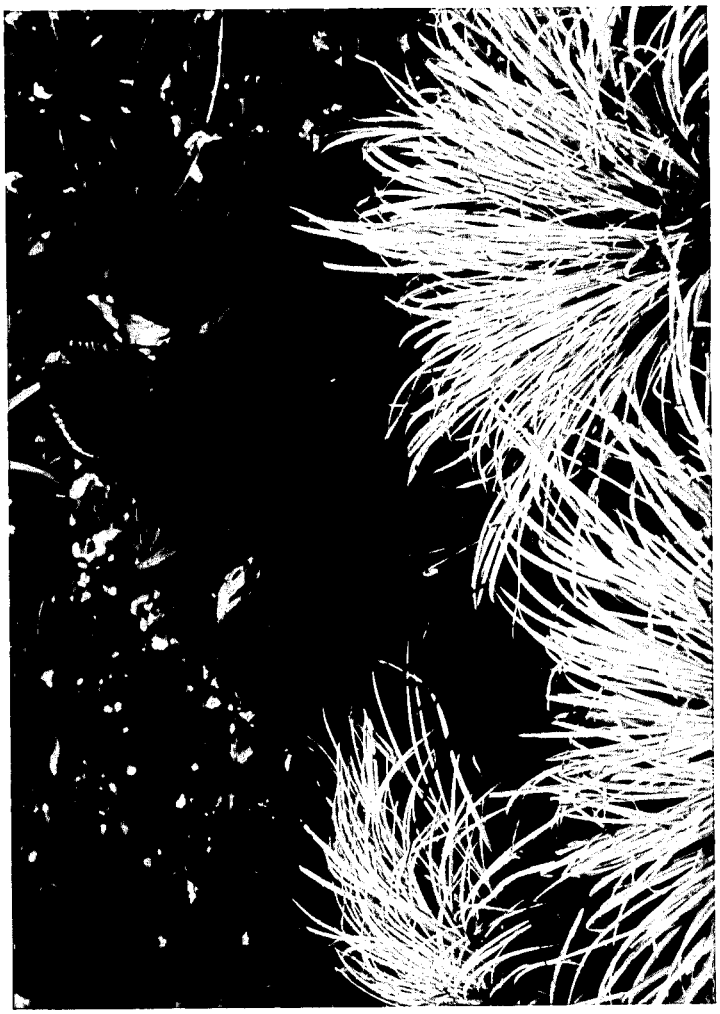
FIG. 1 is a planting of the new variety showing the deep brown to red-brown winter color on the tops of the leaves with lighter purple color under leaf.
Figure 2:
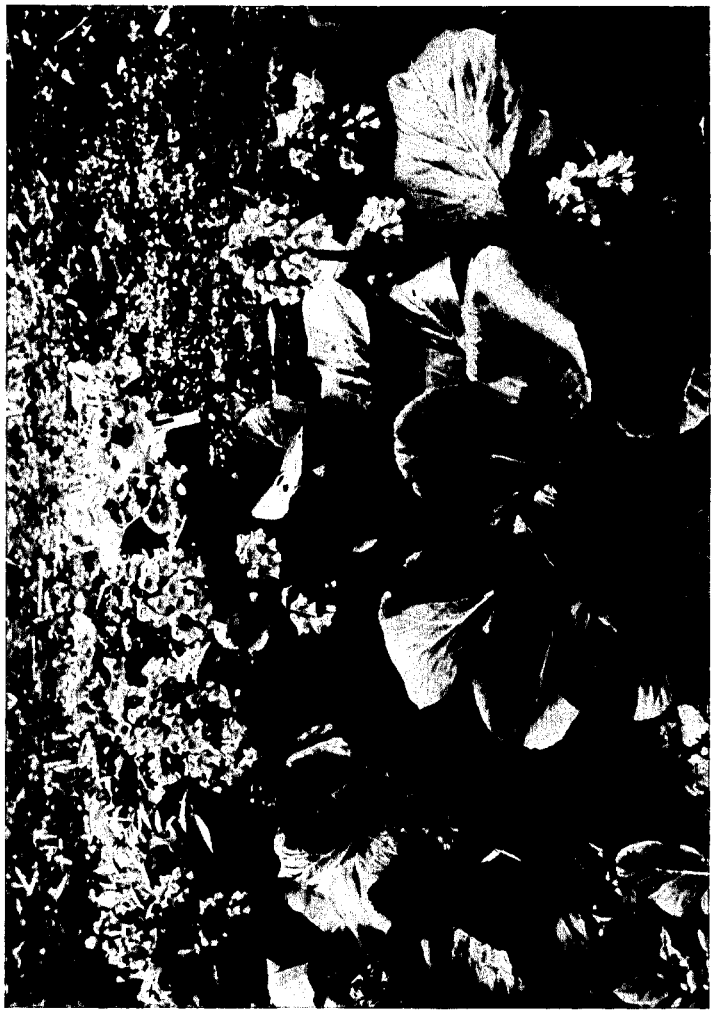
FIG. 2 is an early spring overview of a mixture of leaf colors from older leaves with slight bronzing on the margins to younger leaves with a fresh bright green color. Clusters of flowers are on purple-red stems.
Figure 3:
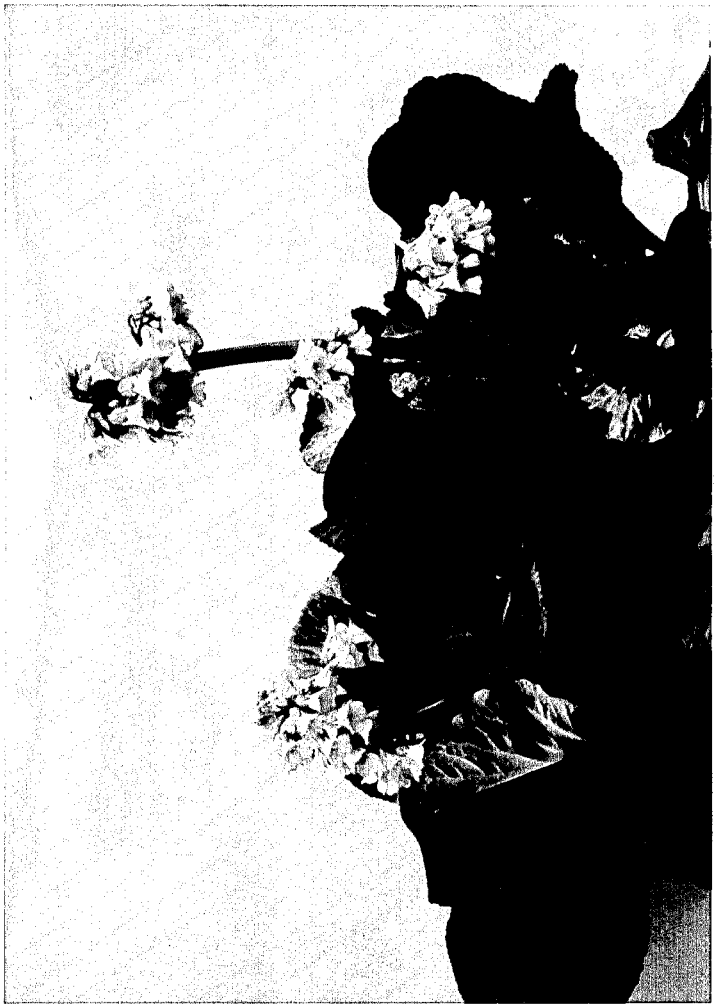
FIG. 3 shows the deep green foliage and attractive flowers of a plant approximately one year old in a No. 2 container during early spring.

*Bergenia purpurescens* is described by Bailey as having "elliptic or ovate-elliptic leaves which are diffused with purple." Brown describes the leaves as "more or less shaded purplish red." Harper describes the leaves as "bronze-flushed." As shown in FIG. 3, the leaves of this Bergenia hybrid are green during the non-winter months. Adrian Bloom indicates that this parent is less hardy than the hybrid.

Bailey does not note any winter coloring in his description of *Bergenia cordifolia.* Brown describes the leaves to be "usually constantly green." Busse Gardens' catalog lists the cordifolia species as having green leaves. Busse Gardens' catalog lists several cordifolia cultivars which show winter coloring. *B. cordifolia* 'Evening Bells' and *B. cordifolia* 'Sunningdale' are both described with red winter foliage. Adrian Bloom notes that *B. cordifolia* 'Sunningdale' is not as cold hardy and does not have as intense winter color as the new hybrid. The new hybrid is larger than *B. cordifolia* 'Evening Glow,' has single rather than semi-double flowers, and has a more intense winter foliage color than does 'Evening Glow.' Walters Gardens and Matterhorn Nursery both describe *B. cordifolia* 'Perfect' which has purplish-brown leaves during the growing season as well as during the winter. Neither the species or the described cultivars have the green leaves during the growing season followed by the brown to greyed-purple winter color that is unique to this hybrid.

References

1. Bailey, L. H. & E. Z., 1976, *Hortus Third,* Macmillan, New York.
2. Blooms *Wholesale Catalogue* 1978-8, Diss, England (also conversations with Adrian Bloom)
3. Brown, E., 1986, *Landscaping With Perennials,* Timber Press, Portland, Oreg.
4. Busse Gardens *Perennials 1988 Catalog,* Cokato, Minn.
5. Harper & McGourty, 1985, *Perennials How to Select, Grow and Enjoy,* HPBooks, Tucson, Ariz.
6. Horn, M., Matterhorn Nursery, Inc., *1988 Perennial Catalog*
7. Still, S., 1988, *Manual of Herbaceous Ornamental Plants,* Stipes Publishing, Champaign, Ill.
8. Walters Garden, Inc., *Hardy Field Grown Perennials,* Fall 1988/Spring 1989 Catalog, Zeeland, Mich.

We claim:

1. A new and distinct hybrid of Bergenia substantially as shown and described, characterized by:

an attractive and unique winter foliage color; with leaves turning to a deep brown in winter followed by a burgundy red color in late winter.

* * * * *